United States Patent [19]

McCall

[11] Patent Number: 4,577,021

[45] Date of Patent: Mar. 18, 1986

[54] 1H-2-BENZOPYRAN-1-YL ALKYL ON 1-(ISOCHROMAN-1-YL)ALKYL PIPERAZINES

[75] Inventor: John M. McCall, Kalamazoo, Mich.

[73] Assignee: The Upjohn Company, Kalamazoo, Mich.

[21] Appl. No.: 718,199

[22] Filed: Apr. 1, 1985

Related U.S. Application Data

[63] Continuation of Ser. No. 26,719, Apr. 4, 1979, abandoned, which is a continuation-in-part of Ser. No. 847,350, Oct. 31, 1977, abandoned.

[51] Int. Cl.[4] .................. C07D 405/06; C07D 413/06
[52] U.S. Cl. .................................... 544/376; 544/151; 546/196; 549/399; 549/407

[58] Field of Search ................ 544/376, 151; 546/196; 549/399, 407

[56]  References Cited

U.S. PATENT DOCUMENTS

| 3,467,675 | 9/1969 | Petersen et al. | 544/151 |
| 4,066,648 | 1/1978 | Oka et al. | 544/151 |
| 4,487,774 | 12/1984 | McCall | 544/376 |

Primary Examiner—Donald G. Daus
Assistant Examiner—Stephen M. Kapner
Attorney, Agent, or Firm—Sidney B. Williams, Jr.; Joan Thierstein

[57]  ABSTRACT 1H-2-benzopyran-1-yl alkyl or 1-(isochroman-1-yl) alkyl 4-phenyl piperazines are prepared and exhibit antipsychotic and hypotensive activity.

14 Claims, No Drawings

1H-2-BENZOPYRAN-1-YL ALKYL ON 1-(ISOCHROMAN-1-YL)ALKYL PIPERAZINES

DESCRIPTION

Cross Reference to Related Application

This application is a continuation of Ser. No. 026,719 filed Apr. 4, 1979, now abandoned, which is a continuation-in-part of application Ser. No. 847,350 filed Oct. 31, 1977, now abandoned.

SUMMARY OF THE INVENTION

The present application relates to novel compounds which are amines of certain isochromans. In particular the present invention relates to the novel isochromans disclosed in U.S. Ser. No. 858,303, now pending issued as a U.S. Pat. No. 4,153,612, the disclosure of which is incorporated here by reference.

In particular, U.S. Ser. No. 858,303 now U.S. Pat. No. 4,153,612 describes the use of certain isochromans as intermediates for preparing isochroman amine type compounds. With respect to the specification of U.S. Ser. No. 858,303, now U.S. Pat. No. 4,153,612 particular reference is made to Tables 14 and 15 therein.

Moreover, the examples 20, 21a, 21b and 21c provide examples of preparation of amines according to formulas of Tables 14 and 15 therein. Accordingly, there are described:

4-(4-chlorophenyl)-1-[(3,4-dihydro-6,7-dimethoxy-4,4-dimethyl-1H-2-benzopyran-1-yl)methyl]-1,2,3,6-tetrahydropyridine, monohydrochloride in Example 20;

1-[3-(3,4-dihydro-6,7-dimethoxy-1-methyl-1H-2-benzopyran-1-yl)propyl]-4-(4-fluorophenyl)-piperazine, dihydrochloride in Example 21a;

1-[2-(6,7-dimethoxy-4,4-dimethylisochroman-1-yl)ethyl]-4-(3-trifluoromethylphenyl)piperazine, dihydrochloride in Example 21b; and 2-[2-[(6,7-dimethoxy-4,4-dimethylisochroman-1-yl)ethyl]]-6,7-dimethoxy-1,2,3,4-tetrahydroisoquinoline monohydrochloride in Example 21c.

As indicated in the text associated with Table 14 in U.S. Ser. No. 858,303, now U.S. Pat. No. 4,153,612 the method of preparing the isochroman amine type compounds of Table 14 is in the manner of Examples 20, 21a and 21b from the appropriate (6,7-dimethoxy-isochroman-1-yl)alkyl halides and the appropriate amines. Likewise, certain additional isochroman amine type compounds represent novel chemical entities comprising one aspect of the present invention. Moreover, these novel compounds are prepared by following procedures similar to those of Examples 20, 21a and 21b in U.S. Ser. No. 858,303, now U.S. Pat. No. 4,153,612 but substituting the appropriate (6,7-dimethoxyisochroman-1-yl)alkyl halides and the appropriate amines. (TABLE I).

TABLE I

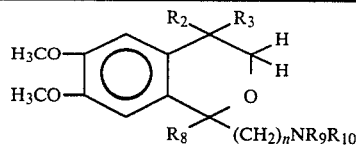

| HNR$_9$R$_{10}$ | n | R$_2$ | R$_3$ | R$_8$ | °C./Hrs. | Misc. | M.P.(°C.) | Anal. (Found) | Name |
|---|---|---|---|---|---|---|---|---|---|
| H—N⟨⟩—C(=)—⟨phenyl⟩ | 3 | H | H | CH$_3$ | | | 197–199$^a$ | | 4-phenyl-1-[3-(3,4-dihydro-6,7-dimethoxy-1-methyl-1H—2-benzopyran-1-yl)propyl]-1,2,3,6-tetrahydropyridine. |
| H—N⟨piperazine⟩N—⟨2-Cl-phenyl⟩ | 2 | H | CH$_3$ | H | | | 170–172$^d$ decomposes | | 4-(2-chlorophenyl)-1-[2-(3,4-dihydro-6,7-dimethoxy-4-methyl-1H—2-benzopyran-1-yl)ethyl]piperazine. |
| H—N⟨piperazine⟩N—⟨2-pyridyl⟩ | 3 | H | H | CH$_3$ | | | 230–231° C. | as mono MeOH.HCl C, 58.31; H, 7.10; N, 8.14; Cl, 13.75 | 4-(2-pyridyl)-1-[3-(3,4-dihydro-1-methyl-6,7-dimethoxy-1H—2-benzopyran-1-yl)-propyl]piperazine. |
| H—N⟨piperazine⟩N—⟨phenyl⟩ | 2 | CH$_3$ | H | H | | | 190–191$^d$ | C, 50.95; H, 7.32; N, 6.22; Cl, 14.86 | 4-phenyl-1-[2-(3,4-di-hydro-6,7-dimethoxy-4-methyl-1H—2-benzopyran-1-yl)ethyl]piperazine. |

TABLE I-continued

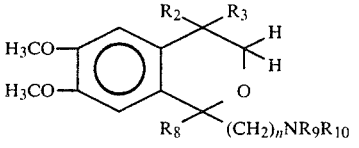

| HNR₉R₁₀ | n | R₂ | R₃ | R₈ | °C./Hrs. | Misc. | M.P.(°C.) | Anal. (Found) | Name |
|---|---|---|---|---|---|---|---|---|---|
| 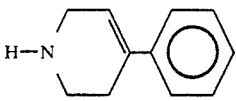 | 2 | CH₃ | H | H | | | 202–204[a] | C, 69.49; H, 7.63; N, 2.98; Cl, 8.35 | 4-phenyl-1-[2-(3,4-di-hydro-6,7-dimethoxy-4-methyl-1H—2-benzopyran-1-yl)ethyl]-1,2,3,6-tetrahydropyridine. |
| 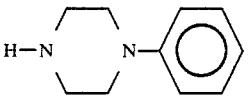 | 3 | CH₃ | CH₃ | CH₃ | | | 225–227[d] | C, 63.79; H, 7.93; N, 5.53; Cl, 13.01 | 4-phenyl-1-[3-(3,4-di-hydro-6,7-dimethoxy-1,4,4-trimethyl-1H—2-benzopyran-1-yl)-propyl]-piperazine. |
| 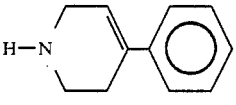 | 3 | CH₃ | CH₃ | CH₃ | | | 221–223[b] | C, 70.43; H, 7.80; N, 2.93; Cl, 7.70 | 4-phenyl-1-[3-(3,4-di-hydro-6,7-dimethoxy-1,4,4-trimethyl-1H—2-benzopyran-1-yl)-propyl]-1,2,3,6-tetrahydropyridine. |
| 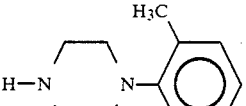 | 3 | CH₃ | CH₃ | CH₃ | | | 223–225[a] | C, 68.44; H, 8.28; N, 5.47; Cl, 7.02 | 4-(2-methylphenyl)-1-[3-(3,4-dihydro-6,7-dimethoxy-1,4,4-trimethyl-1H—2-benzopyran-1-yl)-propyl]piperazine. |
| 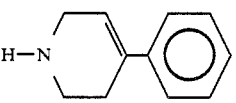 | 3 | CH₃ | CH₃ |  | | | 112–115[c] | C, 69.21; H, 7.36; N, 2.48; Cl, 6.66 | 4-phenyl-1-[3-[1-(4-fluorophenyl)-3,4-dihydro-6,7-dimethoxy-4,4-dimethyl-1H—2-benzopyran-1-yl]propyl]-1,2,3,6-tetrahydropyridine. |
| 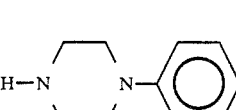 | 3 | CH₃ | CH₃ | CH₃ | | | 231–233[g] | C, 60.72; H, 7.30; N, 5.14; Cl, 12.91; F, 5.24 | 4-(4-fluorophenyl)-1-[3-(3,4-dihydro-6,7-di-methoxy-1,4,4-trimethyl-1H—2-benzopyran-1-yl)-propyl]piperazine. |
| 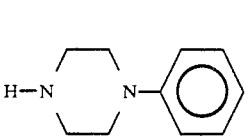 | 3 | CH₃ | CH₃ |  | | | 225–227[c] | C, 66.86; H, 7.21; N, 4.97; Cl, 7.17; F, 3.22 | 4-phenyl-1-[3-[1-(4-fluorophenyl)-3,4-dihydro-6,7-di-methoxy-4,4-dimethyl-1H—2-benzopyran-1-yl]propyl]-piperazine. |

TABLE I-continued

Structure: H3CO and H3CO substituents on benzene ring fused to a pyran with R2, R3, R8, and (CH2)nNR9R10 substituents.

| HNR9R10 | n | R2 | R3 | R8 | °C./Hrs. | Misc. | M.P.(°C.) | Anal. (Found) | Name |
|---|---|---|---|---|---|---|---|---|---|
| 4-phenyl-1,2,3,6-tetrahydropyridine (HN-) | 3 | CH₃ | H | 4-fluorophenyl | | | 220–223[a] | C, 71.06; H, 6.96; N, 2.91; Cl, 6.56; F, 3.52 | 4-phenyl-1-[3-[1-(4-fluorophenyl)-3,4-dihydro-6,7-dimethoxy-4-methyl-1H—2-benzopyran-1-yl]propyl]-1,2,3,6-tetrahydropyridine. |
| 4-phenyl-1,2,3,6-tetrahydropyridine | 3 | CH₃ | H | CH₃ | | | 187–189[b] | C, 69.91; H, 7.55; N, 3.14; Cl, 8.03 | 4-phenyl-1-[3-(3,4-dihydro-6,7-dimethoxy-1,4-dimethyl-1H—2-benzopyran-1-yl)propyl]-1,2,3,6-tetrahydropyridine. |
| 1-(4-fluorophenyl)piperazine | 3 | CH₃ | H | 4-fluorophenyl | | | 254–256[a] | C, 68.66; H, 7.12; N, 5.09; Cl, 6.76; F, 3.52 | 4-phenyl-1-[3-[1-(4-fluorophenyl)-3,4-dihydro-6,7-dimethoxy-4-methyl-1H—2-benzopyran-1-yl]propyl]piperazine. |
| 1-(2-methylphenyl)piperazine | 3 | CH₃ | H | CH₃ | | | 209–211[a] | C, 67.70; H, 8.26; N, 6.32; Cl, 7.55 | 4-(2-methylphenyl)-1-[3-(3,4-dihydro-6,7-dimethoxy-1,4-dimethyl-1H—2-benzopyran-1-yl)propyl]piperazine. |
| 1-(2-chlorophenyl)piperazine | 2 | CH₃ | CH₃ | H | | | 148–149.5[d] | C, 57.29; H, 6.92; N, 5.61; Cl, 20.48 | 4-(2-chlorophenyl)-1-[2-(3,4-dihydro-6,7-dimethoxy-4,4-dimethyl-1H—2-benzopyran-1-yl)ethyl]piperazine. |
| 1-(3-chlorophenyl)piperazine | 2 | CH₃ | CH₃ | H | | | 161–165[a] | C, 61.82; H, 7.09; N, 5.63; Cl, 15.24 | 4-(3-chlorophenyl)-1-[2-(3,4-dihydro-6,7-dimethoxy-4,4-dimethyl-1H—2-benzopyran-1-yl)ethyl]piperazine. |
| 1-(3-chlorophenyl)piperazine | 2 | CH₃ | H | H | | | 115.5–117 | C, 66.65; H, 7.30; N, 6.42; Cl, 8.24 | 4-(3-chlorophenyl)-1-[2-(3,4-dihydro-6,7-dimethoxy-4-methyl-1H—2-benzopyran-1-yl)ethyl]piperazine. |

TABLE I-continued

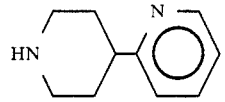

| HNR9R10 | n | R2 | R3 | R8 | °C./Hrs. | Misc. | M.P.(°C.) | Anal. (Found) | Name |
|---|---|---|---|---|---|---|---|---|---|
|  | 3 | H | H | CH3 | | | | | 4-(2-pyridyl)-1-[3-(3,4-dihydro-1-methyl-6,7-dimethoxy-1H—2-benzopyran-1-yl)propyl]piperidine. |
| 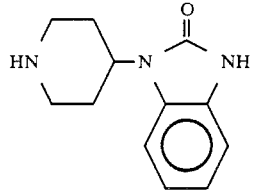 | 2 | CH3 | CH3 | H | | | | | 4-(4-chlorophenyl)-1-[2-(3,4-dihydro-6,7-dimethoxy-4,4-dimethyl-1H—2-benzopyran-1-yl)-ethyl]-1,2,3,6-tetrahydropyridine. |
| 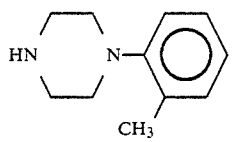 | 2 | CH3 | CH3 | H | | | | | 1-[2-(3,4-dihydro-6,7-dimethoxy-4,4-dimethyl-1H—2-benzopyran-1-yl)ethyl]-piperidin-4-yl]-1,3-di-hydro-2H—benzimidazol-2-one. |

[a] HCl salt
[b] HCl salt hemihydrate
[c] HCl salt hydrate
[d] dihydrochloride salt
[e] dihydrate
[f] trihydrate hydrochloride
[g] dihydrochloride, hemihydrate

TABLE II

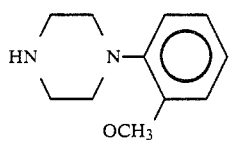

| HNR9R10 | n | R4 | R5 | R8 | °C./Hrs. | Misc. | M.P.(°C.) | Anal. (Found) | Name |
|---|---|---|---|---|---|---|---|---|---|
| (piperazine with 2-methylphenyl) | 2 | CH3 | CH3 | H | | | 222–223[a] | C, 67.77; H, 8.02; N, 6.01 | 4-(2-methylphenyl)-1-[2-(3,4-dihydro-6,7-dimethoxy-3,3-dimethyl-1H—2-benzopyran-1-yl)ethyl]piperazine. |
| (piperazine with 2-methoxyphenyl) | 2 | CH3 | CH3 | H | | | 187–189[d] | C, 60.86; H, 7.68; N, 5.51; Cl, 12.76 | 4-(2-methoxyphenyl)-1-[2-(3,4-dihydro-6,7-dimethoxy-3,3-dimethyl-1H—2-benzopyran-1-yl)ethyl]piperazine. |

TABLE II-continued

[Structure: H₃CO and H₃CO on benzene ring, with H H R₄ R₅ substituents and O, R₈, (CH₂)ₙNR₉R₁₀]

| HNR₉R₁₀ | n | R₄ | R₅ | R₈ | °C./Hrs. | Misc. | M.P.(°C.) | Anal. (Found) | Name |
|---|---|---|---|---|---|---|---|---|---|
| [piperazine-F-phenyl structure: HN-N-⟨⟩-F] | 2 | CH₃ | CH₃ | H | | | 161–163$^b$ | C, 63.20; H, 7.16; N, 6.18 | 4-(4-fluorophenyl)-1-[2-(3,4-dihydro-6,7-dimethoxy-3,3-dimethyl-1H-2-benzopyran-1-yl]ethyl]piperazine. |

$^a$, $^b$, and $^d$ are as defined for TABLE 1.

Compounds of Tables I and II above are within the preferred compounds of U.S. Ser. No. 858,303, now U.S. Pat. No. 4,153,612 Formula I'. Compounds within this group having an alkyl group of one through three carbons at one of the positions R₂ through R₅ or R₈ are more preferred. Further, new compounds of this invention, i.e. 4-(2-chlorophenyl)-1-[2-(3,4-dihydro-6,7-dimethoxy-4,4-dimethyl-1H-2-benzopyran-1-yl)ethyl]piperazine and 4-(3-chlorophenyl)-1-[2-3,4-dihydro-6,7-dimethoxy-4,4-dimethyl-1H-2-benzopyran-1-yl)ethyl]piperazine are among those specifically preferred compounds of Formula I' as defined in U.S. Ser. No. 858,303. In addition compounds prepared herein having alkyls of from one to three carbon atoms, inclusive, at the R₄ and R₅ positions of Formula I', wherein b is zero and R₈ is hydrogen are now also found to be among those specifically preferred in the present invention.

Further, the present invention now comprises the unexpected discovery that certain of the isochroman amine type compounds of U.S. Pat. Ser. No. 858,303 now U.S. Pat. No. 4,153,612 and Tables I and II of this disclosure exhibit a split in activity between an antipsychotic and a hypotensive effect. In other words, such compounds have either first, a high antipsychotic and low cardiovascular effect or second, a low antipsychotic and high cardiovascular effect. The effect of the first split recited above is exhibited by 4-phenyl-1-[2-(3,4-dihydro-6,7-dimethoxy-4,4-dimethyl-1H-2-benzopyran-1-yl)ethyl]-1,2,3,6-tetrahydropyridine monohydrochloride hemihydrate, listed as the eighth compound in Table 14 of U.S. Ser. No. 858,303, 4-phenyl-1-[2-(3,4-dihydro-6,7-dimethoxy-4-methyl-1H-2-benzopyran-1-yl)ethyl]-1,2,3,6-tetrahydropyridine and 4-(2-chlorophenyl)-1-[2-(3,4-dihydro-6,7-dimethoxy-4-methyl-1H-2-benzopyran-1-yl)ethyl]piperazine, the latter compounds are included in Table I herein. The effect of the second split recited above is exhibited by 4-phenyl-1-[3-(3,4-dihydro-6,7-dimethoxy-1-methyl-1H-2-benzopyran-1-yl)propyl]-1,2,3,6-tetrahydropyridine, 4-phenyl-1-[3-(3,4-dihydro-6,7-dimethoxy-1,4,4-trimethyl-1H-2-benzopyran-1-yl)propyl]-1,2,3,6-tetrahydropyridine, 4-phenyl-1-[3-[1-(4-fluorophenyl)-3,4-dihydro-6,7-dimethoxy-4,4-dimethyl-1H-2-benzopyran-1-yl]-propyl]-1,2,3,6-tetrahydropyridine and 4-phenyl-1-[3-(3,4-dihydro-6,7-dimethoxy-1,4-dimethyl-1H-2-benzopyran-1-yl)propyl]-1,2,3,6-tetrahydropyridine, all shown in TABLE I above.

In the formulation of compounds in the present invention for pharmacological utility conventional techniques are used as fully disclosed in U.S. Ser. No. 858,303 now U.S. Pat. No. 4,153,612.

What is claimed is:

1. A compound selected from the group consisting of 4-(2-methylphenyl)-1-[3-(3,4-dihydro-6,7-dimethoxy-1,4-dimethyl-1H-2-benzopyran-1-yl)-propyl]piperazine;
4-(2-methylphenyl)-1-[3-(3,4-dihydro-6,7-dimethoxy-1,4-dimethyl-1H-2-benzopyran-1-yl)-propyl]piperazine, monohydrochloride;
1-[2-(3,4-dihydro-6,7-dimethoxy-4,4-dimethyl-1H-2-benzopyran-1-yl)ethyl]-4-(2-methylphenyl)piperazine;
1-[2-(3,4-dihydro-6,7-dimethoxy-4,4-dimethyl-1H-2-benzopyran-1-yl)ethyl]-4-(2-methylphenyl)piperazine, monohydrochloride;
1-[2-(6,7-dimethoxy-4,4-dimethylisochroman-1-yl)ethyl]-4-(3-trifluoromethylphenyl)piperazine;
1-[2-(6,7-dimethoxy-4,4-dimethylisochroman-1-yl)ethyl]-4-(3-trifluoromethylphenyl)piperazine, dihydrochloride;
4-(2-methylphenyl)-1-[3-(3,4-dihydro-6,7-dimethoxy-1,4,4-trimethyl-1H-2-benzopyran-1-yl)-propyl]piperazine;
4-(2-methylphenyl)-1-[3-(3,4-dihydro-6,7-dimethoxy-1,4,4-trimethyl-1H-2-benzopyran-1-yl)-propyl]piperazine, dihydrochloride;
4-(2-methylphenyl)-1-[3-(3,4-dihydro-1-(4-fluorophenyl)-6,7-dimethoxy-1H-2-benzopyran-1-yl)propyl]piperazine;
4-(2-methylphenyl)-1-[3-(3,4-dihydro-1-(4-fluorophenyl)-6,7-dimethoxy-1H-2-benzopyran-1-yl)propyl]piperazine, hydro-chloride hydrate;
4-(2-methylphenyl)-1-[2-(3,4-dihydro-6,7-dimethoxy-3,3-dimethyl-1H-2-benzopyran-1-yl)-ethyl]piperazine;
4-(2-methylphenyl)-1-[2-(3,4-dihydro-6,7-dimethoxy-3,3-dimethyl-1H-2-benzopyran-1-yl)-ethyl]piperazine, monohydrochloride; and
1-[3-(3,4-dihydro-6,7-dimethoxy-1-methyl-1H-2-benzopyran-1-yl)propyl]-4-(2-methylphenyl)piperazine.

2. A compound of claim 1 for 4-(2-methylphenyl)-1-[3-(3,4-dihydro-6,7-dimethoxy-1,4-dimethyl-1H-2-benzopyran-1-yl)-propyl]piperazine.

3. The monohydrochloride of the compound of claim 2.

4. A compound according to claim 1 for 1-[2-(3,4-dihydro-6,7-dimethoxy-4,4-dimethyl-1H-2-benzopyran-1-yl)ethyl]-4-(2-methylphenyl)-piperazine.

5. The monohydrochloride of the compound of claim 4.

6. A compound according to claim 1 for 1-[2-(6,7-dimethoxy-4,4-dimethylisochroman-1-yl)ethyl]-4-(3-trifluoromethylphenyl)piperazine.

7. The dihydrochloride salt of the compound of claim 6.

8. A compound of claim 1 for 4-(2-methyl-phenyl)-1-[3-(3,4-dihydro-6,7-dimethoxy-1,4,4-trimethyl-1H-2-benzopyran-1-yl)-propyl]piperazine.

9. The dihydrochloride salt of the compound of claim 8.

10. A compound of claim 1 for 4-(2-methylphenyl)-1-[3-(3,4-dihydro-1-(4-fluorophenyl)-6,7-dimethoxy-1H-2-benzopyran-1-yl)propyl]piperazine.

11. The hydrochloride hydrate of the compound of claim 10.

12. A compound of claim 1 for 4-(2-methylphenyl)-1-[2-(3,4-dihydro-6,7-dimethyoxy-3,3-dimethyl-1H-2-benzopyran-1-yl)-ethyl]piperazine.

13. The monohydrochloride of the compound of claim 12.

14. A compound of claim 1 for 1-[3-(3,4-dihydro-6,7-dimethoxy-1-methyl-1H-2-benzopyran-1-yl]-4-(2-methylphenyl)piperazine.

* * * * *